(12) United States Patent
Xu et al.

(10) Patent No.: US 6,627,778 B2
(45) Date of Patent: Sep. 30, 2003

(54) SELECTIVE HYDROGENATION PROCESS FOR REMOVING $C_{10}$-$C_{16}$ DIOLEFINS

(75) Inventors: Yi Xu, Nanjing (CN); Peicheng Wu, Nanjing (CN); Yu Wang, Nanjing (CN); Dong Liu, Nanjing (CN); Zhengguo Ling, Nanjing (CN); Xiaolei Huang, Nanjing (CN)

(73) Assignees: China Petrochemical Corporation, Beijing (CN); Sinopec, Jinling Petrochemical Corporation, Nanjing (CN)

( * ) Notice: Subject to any disclaimer, the term of this patent is extended or adjusted under 35 U.S.C. 154(b) by 0 days.

(21) Appl. No.: 09/837,986

(22) Filed: Apr. 19, 2001

(65) Prior Publication Data
US 2002/0004621 A1 Jan. 10, 2002

(30) Foreign Application Priority Data

Apr. 19, 2000 (CN) ......................................... 00112211 A
Apr. 19, 2000 (CN) ......................................... 00112212 A

(51) Int. Cl.[7] ............................... C07C 5/03; C07C 5/02
(52) U.S. Cl. ........................ 585/260; 585/259; 585/265
(58) Field of Search ................................ 585/254, 260, 585/265

(56) References Cited

U.S. PATENT DOCUMENTS

| 4,520,214 A | * | 5/1985 | Vora | 208/255 |
| 5,281,753 A | * | 1/1994 | Olson et al. | 585/259 |
| 5,498,810 A | * | 3/1996 | Bogdan et al. | 585/310 |

* cited by examiner

Primary Examiner—Thuan D. Dang
(74) Attorney, Agent, or Firm—Pennie & Edmonds LLP

(57) ABSTRACT

The present invention provides an improved selective hydrogenation process for removing $C_{10}$–$C_{16}$ diolefins in the product from dehydrogenation of $C_{10}$–$C_{16}$ paraffins to mono-olefins, which process includes bringing the mixture stream of paraffins and olefins containing $C_{10}$–$C_{16}$ mono-olefins and $C_{10}$–$C_{16}$ diolefins into contact with a specific hydrogenation catalyst in a plurality of hydrogenation reactors connected in series under the reaction conditions for hydrogenation. Hydrogen is injected into each reactor respectively. To convert the diolefins in the mixture stream of paraffins and olefins into mono-olefins, γ-alumina having a specific surface area of 50–300 $m^2/g$ and a pore volume of 0.2–2.0 $cm^3/g$ is used as the supporter of the hydrogenation catalyst, palladium is supported on the supporter as the main catalyst element and an element selected from silver, gold, tin, lead or potassium is supported on the supporter as the promoter.

9 Claims, 1 Drawing Sheet

SELECTIVE HYDROGENATION PROCESS FOR REMOVING $C_{10}$-$C_{16}$ DIOLEFINS

FIELD OF THE INVENTION

The present invention relates to a process for selective hydrogenation of $C_{10}$–$C_{16}$ diolefins in the product from the dehydrogenation of $C_{10}$–$C_{16}$ paraffins to mono-olefins. More particularly, it relates to a process which can simultaneously enhance the conversion and selectivity of selective hydrogenation of $C_{10}$–$C_{16}$ diolefins under mild conditions by using a combination of a specific catalyst with a multi-stage hydrogenation mode

BACKGROUND OF THE INVENTION

The olefin stream produced in the plant for producing the feedstock of the is detergent-linear alkyl benzene by dehydrogenation of $C_{10}$–$C_{16}$ paraffins contains about 1–3 wt % of diolefins. The presence of these diolefins will cause a lot of side reactions in the subsequent alkylation, resulting in a decrease of the yield and quality of alkyl benzene. The quality of alkyl benzene may be effectively improved on the basis of enhancing the yield of alkyl benzene by selective hydrogenation of diolefins in the dehydrogenation product to mono-olefins.

U.S. Pat. Nos. 4,695,560, 4,523,048, 4,520,214, 4,761,509 and Chinese Patent CN 1032157 disclose a process for selective hydrogenation of diolefins in the product from dehydrogenation of $C_8$–$C_{20}$ paraffins. The characteristics of the catalyst in this process are that it contains 1.0–25 wt % of nickel, 0.05–1.5 wt % of sulfur and the supporter is small $Al_2O_3$ balls made by the oil-drop method, which balls have a pore volume of 1.44–3.0 cm$^3$/g, a surface area larger than 150 m$^2$/g and have no precious metals, and essentially have no halogens, alkali earth metals and alkali metals (<0.1 wt %). Because the main active element of the catalyst used in this process is nickel, selective hydrogenation has to be conducted at a temperature higher than 200° C. to attain a certain activity. This would results in the occurrence of the side reaction-cracking and the increase of the consumption of the feed material. Meanwhile, because this process uses a single-stage reaction mode and hydrogen needed by hydrogenation is introduced at one time, the reaction pressure must be retained at above 1.1 MPa to allow hydrogen to fully dissolve in the liquid mixture of paraffins and olefins In addition, in order to increase the selectivity of diolefins, to mono-olefins, it is necessary to frequently sulfurize the catalyst so as to suppress its activity. Sulfurization is a complicated technology and it is difficult to control the amount of sulfur injecting onto the catalyst in operation. If this amount is too large, the activity of the catalyst is very low, while if this amount is insufficient, the selectivity of the catalyst is very poor. Furthermore, the investment will increase due to the equipment of the sulfur-injecting system.

Chinese patent CN 1236333A reports a process for preparing a selective hydrogenation catalyst and its applicable scope, which catalyst contains palladium and at least one element selected from tin and lead. Alumina with a specific surface area of 5–200 m$^2$/g and a pore volume of 0.3–0.95 cm$^3$/g is used as the supporter of the catalyst reported in this patent and at least 80% of the active element, palladium, is distributed within the volume between the surface and the spherical face at the depth of 500 μm of the catalyst particles by impregnation. The promoter elements selected for enhancing the selectivity of the reaction are tin and lead. The catalyst is suitable for selective hydrogenation of lower hydrocarbons such as butadiene, etc., but does not suit selective hydrogenation of $C_{10}$–$C_{16}$ long chain diolefins because both its specific surface area and pore volume are quite small.

U.S. Pat. No. 4,704,492 reports a multi-stage selective hydrogenation process for removing acetylenic impurities from a natural butadiene gas. The characteristic of this process is to effectively decrease the ratio of hydrogen to the compounds to be hydrogenated by separately injecting hydrogen into each stage and thereby effectively enhance the selectivity of hydrogenation.

The objective of the present invention is to effectively remove diolefins, which are the by-products simultaneously generated in dehydrogenation of $C_{10}$–$C_{16}$ paraffins for producing mono-olefins and avoid the shortcomings of the requirements for high temperature and pressure, frequent sulfurization of the hydrogenation catalyst existing in the prior arts which use nickel-containing catalysts.

In order to adapt the requirement of the reaction of $C_{10}$–$C_{16}$ diolefins, γ-alumina with a specific surface area of 50–300 m$^2$/g, a pore volume of 0.2–2.0 cm$^3$/g, is used as a supporter, which allows the long chain mono-olefins to rapidly diffuse in the pores of the catalyst and permits the use of the catalyst in selective hydrogenation of $C_{10}$–$C_{16}$ diolefins. The reaction temperature and pressure can be lowered to a large extent because the activity of palladium-containing catalysts is much higher than that of nickel-containing catalysts. Because a multi-stage hydrogenation process is used, the selectivity and conversion of diolefins to mono-olefins is increased by controlling the hydrogen/diolefin molar ratio and the decrease of the yield due to hydrogenation of mono-olefins to paraffins is avoided, thereby the yield of mono-olefins is increased. The shortcomings of complicated and unstable operation and high investment, etc., resulting from the requirement of the nickel-containing catalysts for sulfurization were avoided as no sulfurization is needed for enhancing the selectivity of diolefins to mono-olefins. Through combining the above several approaches and applying them to selective hydrogenation of $C_{10}$–$C_{16}$ diolefins, the selectivity and conversion of $C_{10}$–$C_{16}$ diolefins to mono-olefins are increased.

SUMMARY OF THE INVENTION

The present invention provides an improved selective hydrogenation process for removing $C_{10}$–$C_{16}$ diolefins in the product from the dehydrogenation of $C_{10}$–$C_{16}$ paraffins to mono-olefins, which process includes bringing the mixture stream of paraffins and olefins containing $C_{10}$–$C_{16}$ mono-olefins and $C_{10}$–$C_{16}$ diolefins into contact with a specific hydrogenation catalyst in a plurality of hydrogenation reactors connected in series under the reaction conditions for hydrogenation The inlet of each reactor has a hydrogen injection pipe respectively and hydrogen is injected into each reactor. To convert diolefins in the mixture stream of paraffins and olefins into mono-olefins by hydrogenation, γ-alumina having a specific surface area of 50–300 m$^2$/g and a pore volume of 0.2–2.0 cm$^3$/g is used as the supporter of the hydrogenation catalyst palladium being supported or the supporter as the main catalyst element and an element selected from silver, gold, tin, lead or potassium being supported on the supporter as the promoter.

DETAILED DESCRIPTION OF THE INVENTION

Figure 1:
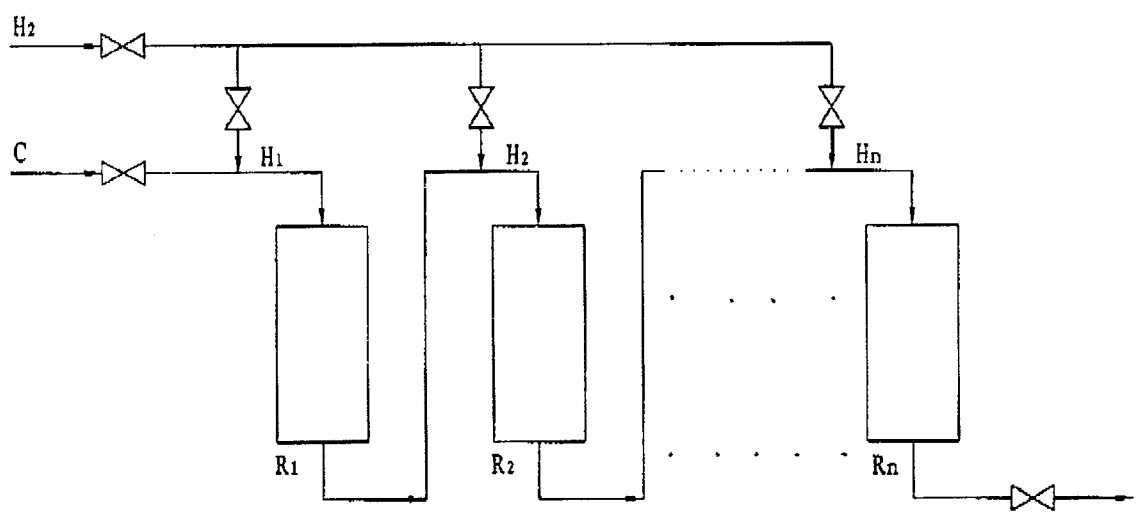
FIG. 1 is the schematic diagram of the multi-stage hydrogenation process of the present invention, wherein R denotes the reactors, H denotes the hydrogen injecting pipes and C denotes the inlet of the mixture stream of paraffins and olefins containing $C_{10}$–$C_{16}$ mono-olefins and $C_{10}$–$C_{16}$ diolefins.

A supporter having a specific surface area of 50–300 m²/g, preferably 100–200 m²/g, a pore volume of 0.2–2.0 cm³/g, preferably 0.5–1.5 cm³/g is provided by rolling pseudo-boehmite powder into balls, drying at 100–200° C. for 1–10 h, and calcining at 300–800° C. for 1–10 h. Palladium is supported on the supporter as a main catalyst element and an element selected from silver, gold, tin, lead or potassium is supported on the supporter as a promoter by impregnation. The impregnated sample is dried at 100–200° C. for 2–8 h and the dried sample is calcined in air at 300–600° C. for 2–8 h. The calcined sample is reduced with hydrogen at a temperature from room temperature to 300° C., preferably 60–150° C. for 0.5–10 h, preferably 1–5 h, and thus the hydrogenation catalyst of the present invention is obtained.

The schematic diagram of the multi-stage hydrogenation process used in the present invention is shown in FIG. 1. The liquid mixture of paraffins and olefins flows in sequence through rectors connected in series $R_1$, $R_2$, ... $R_n$, each of which has a hydrogen injection pipe $H_1$, $H_2$, ... $H_n$ respectively at its inlet. The $H_2$/diolefin molar ratio in each reactor can be adjusted respectively by controlling the amount of hydrogen injected from the inlet of each reactor. The amount of hydrogen injected from the inlet of each reactor respectively is such that the $H_2$/diolefin molar ratio in each reactor respectively is 10–50%, preferably 20–30% of the total $H_2$/diolefin molar ratio of the selective hydrogenation, so that the conversion of mono-olefins to paraffins is suppressed on the basis of fully ensuring the conversion of diolefins to mono-olefins.

The conditions used in selective hydrogenation of $C_{10}$–$C_{16}$ diolefins in the present invention are reaction temperature of 30–250° C., preferably 50–200° C., pressure of 0.1–2.0 MPa, preferably 0.5–1.0 MPa, liquid hourly space velocity of 1–20 h⁻¹, preferably 5–10 h⁻¹, and hydrogen/diolefin total molar ratio of 0.1–5.0, preferably 0.5–2.0.

Applying the combination of the above several approaches to hydrogenation of the mixture stream of paraffins and olefins containing $C_{10}$–$C_{16}$ mono-olefins and $C_{10}$–$C_{16}$ diolefins, hydrogenation may be conducted under mild conditions and the sulfurization is avoided. Therefore, the selectivity and conversion of $C_{10}$–$C_{16}$ diolefins to mono-olefins by hydrogenation is increased and $C_{10}$–$C_{16}$ diolefins contained in said mixture stream of paraffins and olefins are effectively removed, thus the yield of $C_{10}$–$C_{16}$ mono-olefins is increased while enhancing the quality of $C_{10}$–$C_{16}$ mono-olefins product.

The following examples are used to particularly describe the present invention, but not to limit its scope.

EXAMPLES

Example 1

Pseudo-boehmite powder was shaped by rolling ball to form small balls of φ1.8–2.2 mm, which were dried at 120° C. for 5 h and then calcined at 600° C. for 5 h to yield small γ-alumina balls with specific surface area of 220 m²/g, pore volume of 1.5 cm³/g.

Example 2

The process for preparing the supporter was the same as in Example 1. The supporter was first impregnated with 0.85 N solution of $PdCl_2$, dried at 120° C. for 5 h and calcined at 550° C. for 6 h. After dechlorination, the calcined sample was impregnated with 0.5 N solution of $AgNO_3$, dried at 120° C. for 5 h, calcined at 550° C. for 8 h, and reduced with hydrogen having a purity of higher than 99% to yield a catalyst. The catalyst product contains palladium of 0.3 wt % and silver of 1 wt %.

Example 3

The process for preparing the catalyst was the same as in Example 2. 100 l of the prepared catalyst was loaded in one reactor. The reaction temperature was controlled at 130° C., pressure at 0.8 MPa, LHSV at 5.0 h⁻¹, $H_2$/diolefin molar ratio at 1. The conversion of diolefins was 65.5% and the selectivity to mono-olefins was 32.6% after selective hydrogenation of a stream containing 2.5 wt % of $C_{10}$–$C_{14}$ diolefins.

Example 4

The process for preparing the catalyst was the same as in Example 2. 100 l of the prepared catalyst was loaded in 4 reactors averagely and the 4 reactors were used in series. The reaction temperature was controlled at 130° C., pressure at 0.8 MPa, LHSV at 5.0 h⁻¹, $H_2$/diolefin molar ratio at 1. The amount of hydrogen injected into each reactor was ¼ of the total. The conversion of diolefins was 88.0% and the selectivity to mono-olefins was 60.2% after selective hydrogenation of a stream containing 2.5 wt % of $C_{10}$–$C_{14}$ diolefins.

It can be seen from the conditions of hydrogenation used in examples 3 and 4 that hydrogenation of the present invention can be conducted at a mild temperature and pressure due to the adoption of a specific hydrogenation catalyst of the present invention and that the conversion and selectivity of diolefins to mono-olefins are increased due to the adoption of a multi-stage hydrogenation process and the control of $H_2$/diolefin molar ratio in the stream injected into each reactor.

What is claimed is:

1. A selective hydrogenation process for removing $C_{10}$–$C_{16}$ diolefins in a product, which is a mixture of paraffins and olefins that contains $C_{10}$–$C_{16}$ mono-olefins and $C_{10}$–$C_{16}$ diolefins, obtained from dehydrogenation of $C_{10}$–$C_{16}$ paraffins to produce mono-olefins, in said process, $C_{10}$–$C_{16}$ diolefins are selectively hydrogenated to mono-olefins, characterized in that the mixture stream is contacted with a specific hydrogenation catalyst in a plurality of separated hydrogenation reactors connected in series with pipes under the reaction conditions for hydrogenation; the inlet of each reactor has a hydrogen injection pipe respectively and hydrogen is injected into each reactor, wherein the amount of hydrogen injected from the inlet of each reactor respectively is such that the total hydrogen/diolefin molar ration of the selective hydrogenation is 0.5–2.0, and $H_2$/diolefin molar ration; γ-alumina having a specific surface ration of 50–300 m²/g and a pore volume of 0.2–2.0 cm³/g is used as the supporter of the hydrogenation catalyst, palladium being supported on the supporter as the main catalyst element and an element selected from silver, gold, tin, lead or potassium being supported on the supporter as the promoter.

2. The selective hydrogenation process of claim 1, wherein the supporter of the hydrogenation catalyst is prepared in the following method: Pseudo-boehmite powder is used as the feedstock and shaped by rolling ball; the balls are dried at 100–200° C. for 1–10 h and calcinced at 300–800° C. for 1–10 h.

3. The selective hydrogenation process of claim 1, wherein γ-alumina used as the supporter of the hydrogenation catalyst has a specific surface area of 100–200 m²/g, a pore volume of 0.5–1.5 cm³/g.

4. The selective hydrogenation process of any of claims 1, 2, and 3 wherein the hydrogenation catalyst is prepared in the following method: the A main catalyst element palladium is supported onto the γ-alumina supporter by impregnation; a promoter element selected from silver, gold, tin, lead or potassium is supported onto the γ-alumina supporter by impregnation; the impregnated supporter is dried at 100–200° C. for 2–8 h, calcined at 300–600° C. for 2–8 h and reduced with hydrogen at a temperature between the room temperature to 3000° C. for 0.5–10 h.

5. The selective hydrogenation process of claim 4, wherein the temperature in hydrogen reduction is 60–150° C. and the reduction duration is 1–5 h.

6. The selective hydrogenation process of any of claims 1, 2, and 3 wherein the conditions in selective hydrogenation are reaction temperature of 30–250° C., reaction pressure of 0.1–2.0 MPa, liquid hourly space velocity of 1–20 h$^{-1}$.

7. The selective hydrogenation process of claim 6, wherein the conditions in selective hydrogenation are reaction temperature of 50–200° C. reaction pressure of 0.5–1.0 MPa, liquid hourly space velocity of 5–10 h$^{-1}$; total hydrogen/diolefin molar ratio of 0.5–2.0.

8. The selective hydrogenation process of any of claims 1, 2, and 3 wherein the mixture stream of paraffins and olefins containing $C_{10}$–$C_{16}$ straight chain mono-olefins and $C_{10}$–$C_{16}$ diolefins is produced in the process for dehydrogenating $C_{10}$–$C_{16}$ paraffins to produce $C_{10}$–$C_{16}$ straight chain mono-olefins.

9. The selective hydrogenation process of claim 8, wherein the content of $C_{10}$–$C_{16}$ diolefins in the mixture stream of paraffins and olefins is 1–3 wt %.

* * * * *